United States Patent
Toyoshima et al.

(10) Patent No.: US 7,163,530 B1
(45) Date of Patent: Jan. 16, 2007

(54) ABSORBENT MEMBER HAVING THREE DIMENSIONAL GUARDS

(75) Inventors: Haruko Toyoshima, Tochigi (JP); Toshiaki Ichimata, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/019,650

(22) PCT Filed: Nov. 2, 2000

(86) PCT No.: PCT/JP00/07755

§ 371 (c)(1),
(2), (4) Date: Jan. 3, 2002

(87) PCT Pub. No.: WO01/34084

PCT Pub. Date: May 17, 2001

(30) Foreign Application Priority Data

Nov. 10, 1999 (JP) .................................. 11-320341

(51) Int. Cl.
*A61F 13/15* (2006.01)
*A61F 13/20* (2006.01)

(52) U.S. Cl. .......................... 604/385.28; 604/385.27; 604/385.01

(58) Field of Classification Search ........... 604/385.01, 604/385.24–385.3
See application file for complete search history.

(56) References Cited

U.S. PATENT DOCUMENTS 4,246,900 A * 1/1981 Schroder .................. 604/368
5,397,318 A * 3/1995 Dreier .................... 604/385.19
5,558,660 A * 9/1996 Dreier .................... 604/385.19
5,624,426 A * 4/1997 Roe et al. ............... 604/385.28
5,776,121 A * 7/1998 Roe et al. ............... 604/385.25
6,156,023 A * 12/2000 Yoshioka ................ 604/385.29
6,248,098 B1 * 6/2001 Sayama .................. 604/385.28
6,562,017 B1 * 5/2003 Nakaoka et al. ....... 604/385.28
6,624,340 B1 * 9/2003 Mizutani et al. ............ 604/358

FOREIGN PATENT DOCUMENTS

| JP | 62-250201 A | 10/1987 |
| JP | 3-90149 A | 4/1991 |
| JP | 4-152947 A | 5/1992 |
| JP | 7-112003 A | 5/1995 |
| JP | 7-71567 | 8/1995 |
| JP | 2001-025485 A | 1/2001 |
| WO | WO 97/12571 | * 4/1997 |

* cited by examiner

*Primary Examiner*—Michele Kidwell
(74) *Attorney, Agent, or Firm*—Birch, Stewart, Kolasch & Birch, LLP

(57) ABSTRACT

An absorbent article which is provided with a liquid permeable surface sheet (2), a liquid impermeable leakage-prevention sheet (3) and a liquid-retaining absorbent (4) interposed between the sheets, is formed substantially oblong, and is provided on the longitudinal opposite sides thereof with a pair of right and left, elastic member-carrying three-dimensional guards (5), (5), wherein the guards (5) each has a skin-contacting surface portion (5A) formed by folding back a side on the free end (53) toward the outer side of the diaper, and elastic members in a stretched condition are respectively disposed and fixed to the skin-contacting surface portion (5A) and to the approximately widthwise central portion of a raised portion (5B) between the skin-contacting surface portion (5A) and the base end (52) of a three-dimensional guard body.

11 Claims, 3 Drawing Sheets

ABSORBENT MEMBER HAVING THREE DIMENSIONAL GUARDS

This application is the national phase under 35 U.S.C. § 371 of PCT International Application No. PCT/JP00/07755 which has an International filing date of Nov. 2, 2000, which designated the United States of America.

TECHNICAL FIELD

This invention relates to an absorbent article such as a disposable diaper which is excellent in leakage prevention property and feel during wear.

BACKGROUND ART

Various disposable diapers are proposed which are each provided with a liquid-permeable surface sheet, a liquid impermeable leakage-prevention sheet and a liquid-retaining absorbent, which are each formed substantially oblong, and which are each provided on the longitudinal opposite sides thereof with a pair of right and left elastic member-carrying three-dimensional guards.

Normally, the three-dimensional guards of such disposable diapers are each provided at the free end thereof with a string-like elastic member so as to raise upward.

With this construction, however, a problem is encountered in which a distal end of each three-dimensional guard, when the diaper is in wear, is liable to enter inwardly of the diaper, thereby readily allowing the discharged wastes to ride across the three-dimensional guards and leak from the sides. Moreover, since the distal ends of the three-dimensional guards give hard touch to the skin of the wearer, the feel during wear is not good.

Japanese Patent Publication No. 07-71567 discloses a disposable diaper in which a part of each three-dimensional guard comes into surface abutment with the wearer. In this diaper, however, since the three-dimensional guard is not sufficiently raised, no sufficient space for retaining the discharged wastes is formed at the inside (between the three-dimensional guard and the surface sheet) of the three-dimensional guard and the leakage prevention property is not satisfactory.

Japanese Patent Application Laid-Open Publication No. 04-152947 discloses a disposable diaper in which elastic members are respectively disposed on the free end of the three-dimensional guard and at the widthwise middle of the three-dimensional guards, such that the elastic member disposed on the free end is located at the side part of the diaper and the elastic member disposed on the widthwise middle is located at the inner side of the diaper. In this diaper as well, however, since the three dimensional guard, especially the section between the base end of the three-dimensional guard and the middle where the elastic member is disposed is not sufficiently raised, no sufficient space for retaining the discharged wastes is formed at the inside of the three-dimensional guard and the leakage prevention property is not sufficient.

DISCLOSURE OF INVENTION

Accordingly, it is an object of the present invention to provide an absorbent article such as a disposable diaper, in which the three-dimensional guards have a favorable raising property and give a nice fit (intimate contact property) to the wearer's skin, and in which the leakage prevention property and the feel during wear are excellent.

The above object has been achieved by providing an absorbent article which is provided with a liquid permeable surface sheet, a liquid impermeable leakage-prevention sheet and a liquid-retaining absorbent is formed substantially oblong, and is provided on longitudinal opposite sides thereof with a pair of right and left, elastic member-carrying three-dimensional guards, wherein the three-dimensional guards each has a skin-contacting surface portion formed by folding back a side on a free side towards the outer side of the absorbent article, and the elastic members are respectively disposed and fixed to the skin-contacting surface portion and to an approximately widthwise central portion of a raised portion between the skin-contacting surface portion and a base end of the three-dimensional guard.

BEST MODE FOR CARRYING OUT THE INVENTION

Figure 1:
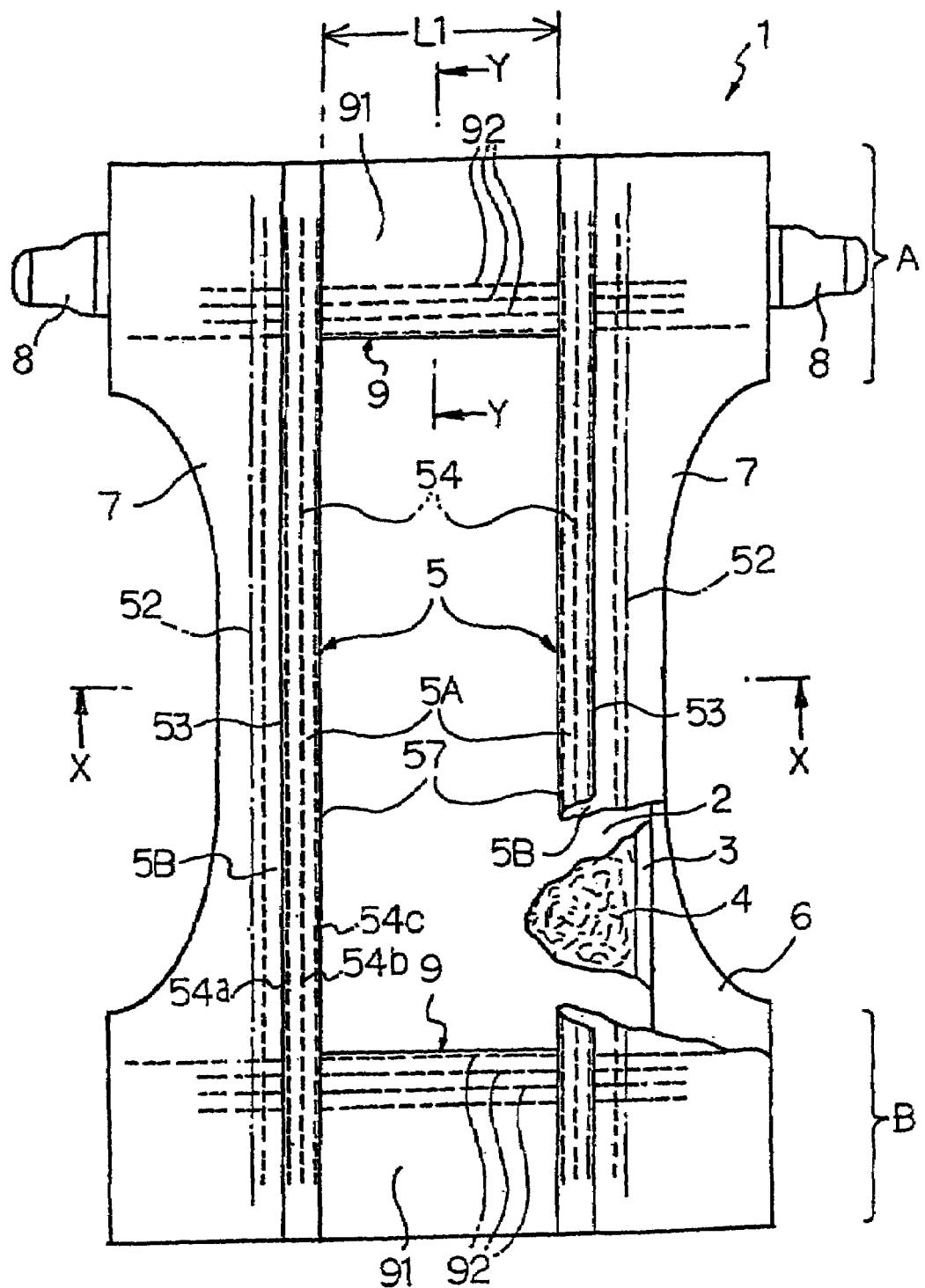
FIG. 1 is a plan view, when viewed from the surface sheet side (skin-contacting surface portion side) of a disposable diaper according to one embodiment of the present invention, in which the elastic members are in stretched condition.

One preferred embodiment of the present invention will be described hereinafter.

A disposable diaper 1 as an absorbent article of this embodiment is provided with a liquid permeable surface sheet 2, a liquid impermeable, leakage-prevention sheet 3 and a liquid-retaining absorbent 4 interposed between the sheets, is formed substantially oblong, and is provided on the longitudinal opposite sides thereof with a pair of right and left, elastic member-carrying three-dimensional guards 5, 5.

The surface sheet 2 and the leakage-prevention sheet 3 each has an oblong configuration and are joined to each other at a peripheral edge extending outward of the absorbent 4. The absorbent 4 has an oblong configuration and is sandwiched and fixed between the surface sheet 2 and the leakage-prevention sheet 3.

An outer layer non-woven fabric 6 is disposed in the leakage-prevention sheet 3 on the surface which is not brought into contact with wearer's skin. The outer layer non-woven fabric 6 is extended such that the opposite side edges thereof are located at a rather more out side portion than a side edge 4a of the absorbent 4 (e.g., see FIG. 2). This extended portion is adhered to a sheet material 51 for forming the three-dimensional guards, thereby forming a pair of right and left side flap portions 7. A back side portion A is provided at opposite side edge portions thereof with a pair of right and left fastening tapes 8, 8.

Figure 2:
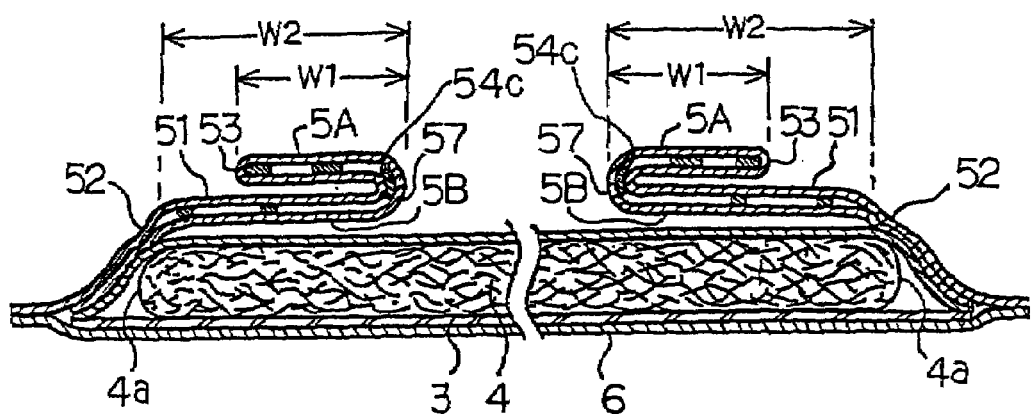
FIG. 2 is a sectional view taken on line X—X of FIG. 1.

The three-dimensional guards 5 are, as shown in FIG. 2, formed by disposing sheet materials 51, 51 for forming the three-dimensional guards on the longitudinal opposite sides of the diaper 1. Each sheet material 51 is disposed toward the inner side of the diaper from each side edge. The sheet material 51 is joined to the surface sheet 2 at an upper part of the side edge portion of the absorbent 4, thereby forming a base end 52 of the three-dimensional guard 5.

A sheet material 91 for forming a waist three-dimensional guard and having a plurality of elastic member 92, 92 are disposed on longitudinal opposite end portions of the diaper 1, thereby forming waist three-dimensional guards 9, 9.

Each three-dimensional guard 5 in the disposable diaper 1 has a skin-contacting surface portion 5A formed by folding back a side portion on the free end 53 side toward the outer side of the diaper.

More specifically, the side portion on the free end 53 side of the three-dimensional guard 5 is folded back over the longitudinal overall area of the diaper 1. On the longitudinal opposite end portions of the diaper, the three-dimensional guard 5 is joined and fixed onto the waist three-dimensional guard forming sheet material 91 with the thus folded back side portion on the free end 53 side of the three-dimensional guard 5. A region of the three-dimensional guard 5 widthwise ranging from the folded back portion 57 to the free end 53 between the back side portion A and the back side portion B of the diaper forms the skin-contacting surface portion 5A which comes into surface contact with the skin of the wearer when the diaper is in wear.

The skin-contacting surface portion 5A is folded back at a part of the location of the elastic member 54c nearest to the raised portion 5B along the elastic member 54c. Since the skin-contacting surface portion 5A is folded back along the elastic member 54c, the skin-contacting surface portion 5A can easily take a free angle with respect to the raised portion 5B in conformity to the movement of the wearer. For this reason, the fitness of the three-dimensional guard 5 to the wearer is enhanced and an even more excellent leakage prevention effect can be obtained. The folded back portion 57 serving as a boundary between the skin-contacting surface portion 5A and the raised portion 5B is located more on an inner side of a central side than the opposite right and left side edges 4a of the absorbent 4.

Elastic members in a stretched condition are respectively disposed and fixed to the skin-contacting surface portion 5A and to the approximately widthwise central portion of the raised portion 5B between the skin-contacting surface portion 5A and the base end 52 of a three-dimensional guard.

A plurality of elastic members are disposed on and fixed to the skin-contacting surface portion 5A at a predetermined interval and along the free end 53. In the illustrated example, three flat rubbers (shown by reference numerals 54a, 54b and 54c of FIG. 1 in order) in total are disposed at a location near to the free end 53 of the skin-contacting surface portion 5A, at the widthwise central portion of the skin-contacting surface portion 5A and at the boundary (in the vicinity of the folded back portion 57) between the skin-contacting surface portion 5A and the raised portion 5B. In the absorbent article of the present invention, the arrangement of the elastic member at the widthwise central portion of the skin-contacting surface portion 5A as in the flat rubber 54b of the illustrated example is preferable in view of the nice fitness (intimate contact property) of the skin-contacting surface portion 5A to the skin of the wearer.

A plurality of elastic members are disposed on and fixed to the raised portion 5B at a predetermined interval and along a longitudinal direction of the diaper 1. In the illustrated example, two flat rubbers (shown by reference numerals 54d and 54e of FIG. 4 in order) in total are disposed on the approximately widthwise central portion of the raised portion 5B and at an area in the vicinity of the base end 52.

In the absorbent article of the present invention, the elastic member, as the flat rubber 54d of the illustrated example, is disposed on the approximately widthwise central portion (preferably at the widthwise central portion) of the raised portion 5B.

In the disposable diaper 1 of this embodiment, the total width of the elastic member disposed on the skin-contacting surface portion 5A is larger than the total width of the elastic member disposed on the raised portion 5B. Owing to this arrangement, a more nice fit (intimate contact property) of the skin-contacting surface portion 5A to the skin of the wearer can be offered.

The expression "total width of the elastic member" used herein refers to the width of the elastic member in the case where only one elastic member is disposed and to the total of the widths of the individual elastic members in the case where a plurality of elastic members are disposed. The width of each elastic member is measured along the surface of the three-dimensional guard.

In this embodiment, the stress of the skin-contacting surface portion 5A is set to larger than the stress of the raised portion 5B.

Specifically, the elastic members 54a, 54b, 54c on the skin-contacting surface portion 5A are disposed on an approximately same elongation rate as the elastic members 54d, 54e on the raised portion 5B but the thickness of the elastic members 54a, 54b, 54c on the skin-contacting surface portion 5A is larger than the thickness of the elastic members 54d, 54e on the raised portion 5B. Moreover, since the elastic members 54a, 54b, 54c on the skin-contacting surface portion 5A are disposed at a smaller interval than the elastic members 54d, 54e on the raised portion 5B. Accordingly the stress of the skin-contacting surface portion 5A is larger than the stress of the raised portion 5B.

The stress of the skin-contacting surface portion 5A is preferably 10 to 200 gf in view of the nice fit (intimate contact property) to the wearer's skin, and the stress of the raised portion 5B is preferably 5 to 18 gf in view of the formation of a sufficient space at an inner side of the three-dimensional guard. The difference between the stress of the skin-contacting surface portion 5A and the stress of the raised portion 5B is preferably 10 gf or more at the time of 100% elongation and particularly preferably 30 to 100 gf in view of, among others, the intimate contact property to the wearer's skin.

As seen, by making the stress of the skin-contacting surface portion 5A larger than the stress of the raised portion 5B, the intimate contact property of the skin-contacting surface portion to the wearer's skin can be more enhanced and the raising property of the raised portion can be sufficiently maintained.

The ratio between the stress of the skin-contacting surface portion 5A and the stress of the raised portion 5B is preferably 101 to 500%, and particularly preferably 105 to 350%. If the ratio of the stress is in this range, the maintenance of the configuration of the raised portion can be enhanced while maintaining the nice fit of the skin-contacting surface portion 5A to the wearer's skin. Accordingly, a pocket structure (space for retaining the excretion) formed on an inner side of the three-dimensional guard is stabilized and the leakage of the discharged wastes can be more restrained.

Furthermore, in this embodiment, where the raised portion 5B is widthwisely bisected into an upper half portion 55 and a lower half portion 56, the stress of the lower half portion 56 is larger than a stress of the upper half portion 55. In the illustrated example, the two elastic members disposed on the raised portion 5B are fixed at an approximately same elongation factor and one of them is located on the upper half portion and the other is located on the lower half portion 56. However, since the thickness of the elastic members 54*d*, 54*e* on the lower half portion 56 is larger than the thickness of the elastic member 54*d* on the upper half portion 55, the stress of the lower half portion 56 is larger than the stress of the upper half portion 55.

Although the disposable diaper of this embodiment has no leg gather on the leg portion, the leg portion can effectively be pulled up toward the wearer's skin by making the stress of the lower half portion 56 on the raised portion 5B larger than the stress of the upper half portion 55 on the raised portion 5B. Thus, the outer appearance of the diaper can be improved. The expression "leg portion" used herein refers to a portion extending outward in the rightward and leftward directions of the longitudinal opposite side edges of the absorbent 4, and the expression "leg gather" used herein refers to a gather formed by disposing the leg elastic member on the leg portion.

The stress of the raised portion 5B and the stress of the upper half portion 55 and the lower half portion 56 on the raised portion 5B can be measured as follows.

The elastic members present in the respective regions the same were cut each having a length of 150 mm, the same was subjected to a tensile test under the conditions of 100 mm in chuck distance and 300 mm/sec in rate of pulling using a Tensilon tensile test machine (manufactured by Orientec Corp.) and the stress at 100% of stretching was measured. The stress (total stress of each elastic member in the case where a plurality of elastic members are had) of the elastic member present in each region was served as the stress of each region.

The ratio (W1/W2) between a width W1 of the skin-contacting surface portion and a width W2 of the raised portion is preferably 0.1 to 1.0 and particularly preferably 0.2 to 0.7 in view of offering the intimate contact property to the wearer's skin and the raising property of the three-dimensional guard simultaneously. The width W1 of the skin-contacting surface portion 5A is preferably 5 to 20 mm, and the width W2 of the raised portion 5B is preferably 20 to 40 mm.

As the material for forming the surface sheet 2, the leakage-prevention sheet 3, the absorbent 4, the three-dimensional guard forming sheet material 51, the outer layer non-woven fabric 6, the fastening tape 8, the waist three-dimensional guard forming sheet material 91 and the waist three-dimensional guard forming elastic member 92 of the diaper 1 of this embodiment, there can be used without any particular limitation those which have heretofore been used for disposable diapers. For example, as the material for forming the three-dimensional guard forming sheet material 51, a water-repellent sheet, a liquid impermeable sheet or a laminated sheet obtained by adhering them, etc. can be used. Of all, the water-repellent sheet is particularly preferable.

As the elastic member 54 disposed on the three-dimensional guard 5, various kinds of normally known elastic members can be used. As such raw material, besides the natural rubber, expansible/contractible raw material such as, synthetic rubber such as styrene-butadiene, butadiene, isoprene and neoprene, EVA, expansible polyolefine, urethane and the like can widely be used. As the form, besides the line-like form of a thread rubber, a wide width belt-like form (including a flat rubber), a thin film-like form, a foam material and the like can be used.

The disposable diaper of this embodiment can be used in the same manner as the normal flat type disposable diaper.

The disposable diaper 1 of this embodiment has the skin-contacting surface portion 5A formed by folding back the side portion on the free end side and the skin-contacting surface portion 5A comes into surface contact with the skin of the wearer. Accordingly, the free end portion of the three-dimensional guard is hardly pulled towards the root of the wearer's leg when the diaper is in wear. For this reason, the excretion leakage from the sides caused by the excretion's riding across the three-dimensional guard can be prevented effectively.

Figure 4:
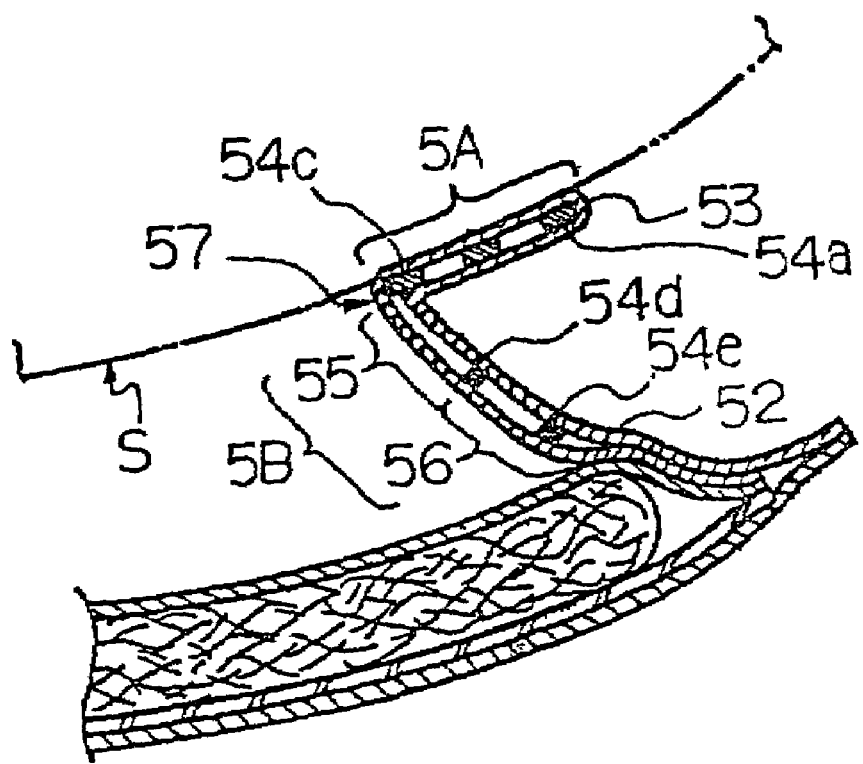
FIG. 4 is a schematic explanatory view showing the condition of the skin-contacting surface portion when the diaper is in use.

Since the elastic members are disposed on an approximately widthwise central portion of the raised portion 5B and the skin-contacting surface portion 5A with the raised portion 5B sufficiently raised is urged against the wearer's skin, the leak of the discharged wastes through the space generated between the wearer's skin and the three-dimensional guard can be prevented more effectively. Moreover, since the skin-contacting surface portion 5A comes into surface contact with the wearer's skin as shown in FIG. 4, it never happens that the elastic members bite into the wearer's skin, the feel during wear is excellent, and the wearer's skin can be prevented from suffering from score and rash.

Moreover, since the elastic members are disposed on an approximately widthwise central portion of the raised portion 5B and the raised portion 5B is sufficiently raised, a space for retaining the excretion is surely formed between the raised portion 5B and the surface sheet 2 and the discharged wastes can be retained in this space. Accordingly, a more enhanced leakage-prevention property can be offered.

The present invention is not limited to the above embodiment. For example, the waist three-dimensional guard can be completely eliminated or it may be disposed on only one end portion, either front or rear end portion in the longitudinal direction of the diaper 1. It is also accepted that the leg gather is formed by disposing the elastic members on the leg portion. The method for making the stress of the skin-contacting surface portion larger than the stress of the raised portion is not particularly limited. This purpose may be achieved by making difference of only one, or two or more of material, thickness, number, interval, elongation factor, etc. The same is likewise applicable in the case where the stress of the lower half portion of the raised portion is made larger than the stress of the upper half portion of the raised portion. The elastic member disposed on the approximately widthwise middle of the raised portion 5B may be a part of the elastic member disposed on the folded back portion 57 and in the vicinity of the base end 52 extending to the approximately widthwise middle of the raised portion.

The present invention can likewise be applied not only to a flat type disposable diaper but also to a shorts type disposable diaper, an incontinent pad, a sanitary napkin and the like.

EXAMPLE 1

Figure 3:
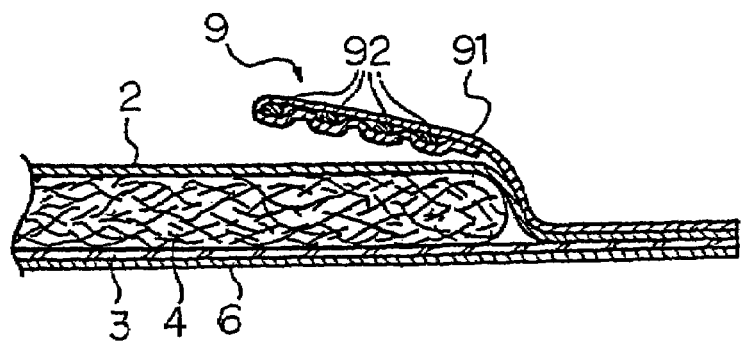
FIG. 3 is a sectional view taken on line Y—Y of FIG. 1.

An outer layer non-woven fabric, a leakage-prevention sheet and a surface sheet were laminated in this order so as to obtain a sectional construction shown in FIG. 2, and a three-dimensional guard forming sheet materials composed of a hydrophobic non-woven fabric and each having five elastic members were folded back and fixed to the surface sheet such that the side on the free end side faces outward. By doing so, a diaper having the construction of FIGS. 1 to 3 was obtained. The width and the stress of the skin-contacting surface portions and of the raised portions of such obtained diaper were measured. The result is shown in Table 1.

EXAMPLE 2

A diaper was manufactured in the same manner as in the Example 1 except that the width and the stress of the skin-contacting surface portions and of the raised portions were changed as in Table 1.

COMPARATIVE EXAMPLE 1

A diaper was manufactured in the same manner as in the Example 1 except that the three-dimensional guard forming sheet materials were fixed to the surface sheets without folding back the side of the free end side. The length from the base end of the three-dimensional guard to the free end was 30 mm.

COMPARATIVE EXAMPLE 2

A commercially available diaper was prepared in which the elastic members were disposed only on the free end of the three-dimensional guard, and leg gathers are formed by disposing the leg elastic members on the side flap portions. The three-dimensional guards of this diaper each have a width of 35 mm and are not folded back.

COMPARATIVE EXAMPLE 3

A diaper was manufactured in the same manner as in the Example 1 only except that the width and the stress of the skin-contacting surface portions and of the raised portions were changed as in Table 1.

In order to check the fitness and leakage-prevention effect of the three-dimensional guard in each diaper of the Examples and the Comparative Examples, evaluation was made with respect to the following items using a dynamic model. The result is shown in Table 1.

[Value of Leakage of Excreta Discharged Through the Crotch]

The obtained diapers were put on an infant model who can move his both legs and in which charged artificial urine and imitation excreta were discharged from the crotch portion. After making him to move the both legs for five minutes, 80 g of an artificial urine was charged in his sitting posture with his legs spread open. Then, making him again to move his both legs for 10 minutes and 40 g of an imitation discharged waste was charged in his sitting posture with his legs spread open. When no leakage occurred in spite of this charge of excreta, additional 40 g of an imitation excreta was charged and further additional 40 g of an imitation excreta was repeatedly charged each time in his sitting posture with his legs spread open until the excreta leaked. The quantity of the imitation excreta charged until the excreta were leaked was served as a value of leakage of excreta discharged through the crotch.

[Excreta Moving Time]

In the same manner of evaluation of the above-mentioned "value of leakage of excreta discharged through the crotch", the excreta moving time was measured in the following manner, with respect to those in which no leakage occurred at the time 40 g of excreta was charged.

That is, after charging 40 g of imitation excreta, the infant model was made to move and the time until leakage occurred was measured. The time until leakage occurred was served as the excreta moving time.

TABLE 1

| | Skin-contacting surface portion | | Raised Portion | | Dynamic Model Evaluation | |
|---|---|---|---|---|---|---|
| | width (mm) | stress (gf) | width (mm) | stress (gf) | value of excreta discharged through the crotch (g) | excreta moving time (min) |
| Ex. 1 | 10 | 65 | 30 | 55 | 120 | 5 |
| Ex. 2 | 15 | 85 | 25 | 35 | 120 | 5 |
| Comp. Ex. 1 | — | — | 30 | 120 | 120 | 2.5 |
| Comp. Ex. 2 | — | — | 35 | 25 | 120 | 2.5 |
| Comp. Ex. 3 | 15 | 50 | 35 | 0 | 80 | 2.5 |

It is known from the result of Table 1 that the diaper (invented article) of each example is excellent in fitness and that since a space for retaining excreta can surely be formed, leakage-prevention property is excellent.

INDUSTRIAL APPLICABILITY

The absorbent article of the present invention is good in raising property of the three-dimensional guard and in fitness (intimate contact property) to the skin of the wearer and excellent in leakage-prevention property and in feel during wear.

The invention claimed is:

1. An absorbent article which is provided with a liquid permeable surface sheet, a liquid impermeable leakage-prevention sheet and a liquid-retaining absorbent is formed substantially oblong,
    wherein said absorbent article is provided on longitudinal opposite sides thereof with a pair of right and left, elastic member-carrying three-dimensional guards,
    wherein said three-dimensional guards each has a skin-contacting surface portion formed by folding back a side on a free side towards an outer side of said absorbent article, and said folded back side forms a folded portion;
        wherein a first set of elastic members are disposed and fixed to said skin-contacting surface portion and a second set of elastic members are disposed and fixed to an approximately widthwise central portion of a raised portion, wherein said raised portion is located between said skin-contacting surface portion and a base end of said three-dimensional guard;
    said raised portion is disposed toward an inner side of the diaper;
    said elastic members in the said second set in the raised portion is fixed between two sheet materials, wherein said two sheet materials form the three-dimensional guard;
    said folded back portion is located between the skin-contacting surface portion and said raised portion; and
    said skin-contacting surface portion is located more on a free end side than the folded back portion, and the region of the guard widthwise ranging from the folded back portion to the free end forms the skin-contacting surface portion.

2. The absorbent article according to claim 1, wherein a total width of said elastic member disposed on said skin-contacting surface portion is larger than a total width of said elastic member disposed on said raised portion.

3. The absorbent article according to claim 1, wherein a ratio (W1/W2) between a width W1 of said skin-contacting surface portion and a width W2 of said raised portion is 0.1 to 1.0.

4. The absorbent article according to claim 1, wherein a stress of said skin-contacting surface portion is larger than a stress of said raised portion.

5. The absorbent article according to claim 1, wherein a leg portion has no leg gather, and when said raised portion is bisected in the width direction into a lower half portion and an upper half portion, a stress of said lower half portion is larger than a stress of said upper half portion.

6. The absorbent article according to claim 1, wherein said skin-contacting surface portion is folded back along said elastic member at a part of the location of said elastic member nearest to said raised portion.

7. The absorbent article according to claim 1, wherein said folded back portion comprises an elastic member that is located between the skin-contacting surface portion and the raised portion.

8. An absorbent article comprising:
   a liquid permeable surface sheet;
   a liquid impermeable leakage-prevention sheet; and
   a liquid-retaining absorbent interposed between said liquid permeable surface sheet and said liquid impermeable leakage-prevention sheet;
   wherein said absorbent article is substantially oblong and comprising a pair of right and left, elastic member-carrying three-dimensional guards located on longitudinal opposite sides thereof;
      wherein each of said three-dimensional guards has a skin-contacting surface portion formed by folding back a side on a free side towards the outer side of said absorbent article; and
      said elastic members are respectively disposed and fixed to each of said portions (i) and (ii):
      (i) said skin-contacting surface portion; and
      (ii) an approximately widthwise central portion of a raised portion, wherein said raised portion is located between said skin-contacting surface portion and a base end of said three-dimensional guard;
   wherein the elastic members in the skin-contacting surface portion of the three-dimensional guard are disposed at a smaller interval relative to the elastic members in the raised portion.

9. The absorbent article according to claim 8, wherein a total width of said elastic members disposed on said skin-contacting surface portion is larger than a total width of said elastic members disposed on said raised portion.

10. The absorbent article according to claim 8, said absorbent article further comprising a waist three-dimensional guard having elastic members disposed on longitudinal opposite end portions.

11. An absorbent article which is provided with a liquid permeable surface sheet, a liquid impermeable leakage-prevention sheet and a liquid-retaining absorbent is formed substantially oblong,
   wherein said absorbent article is provided on longitudinal opposite sides thereof with a pair of right and left, elastic member-carrying three-dimensional guards,
      wherein said three-dimensional guards each has a skin-contacting surface portion formed by folding back a side on a free side towards an outer side of said absorbent article;
      wherein a first set of elastic members are disposed and fixed to said skin-contacting surface portion and a second set of elastic members are disposed and fixed to an approximately widthwise central portion of a raised portion, wherein said raised portion is located between said skin-contacting surface portion and a base end of said three-dimensional guard;
      said raised portion is disposed toward an inner side of the diaper;
      said elastic members in the said second set in the raised portion is fixed between two sheet materials, wherein said two sheet materials form the three-dimensional guard; and
   a folded back portion is located between the skin-contacting surface portion and said raised portion;
   wherein the skin-contacting surface portion is located more on a free end side than the folded back portion, and the region of the guard widthwise ranging from the folded back portion to the free end forms the skin-contacting surface portion.

* * * * *